United States Patent [19]

Janevski et al.

[11] Patent Number: 5,350,418

[45] Date of Patent: Sep. 27, 1994

[54] GEL SHELL SPLINT

[75] Inventors: Peter K. Janevski, Novi, Mich.; Debra A. Reina, Menomonee Falls, Wis.

[73] Assignee: Smith & Nephew Rolyan Inc., Menomonee Falls, Wis.

[21] Appl. No.: 63,888

[22] Filed: May 18, 1993

[51] Int. Cl.$^5$ .............................................. A61F 5/00
[52] U.S. Cl. ..................... 607/111; 607/114; 602/21; 602/43
[58] Field of Search .......... 602/2, 5, 6, 12, 20–23, 602/41–43; 2/161.1, 161.2, 161.3, 161.4, 161.5, 161.6, 162, 16, 20; 607/96, 108, 111, 112

[56] References Cited

U.S. PATENT DOCUMENTS

| | | |
|---|---|---|
| 950,143 | 2/1910 | Saxe . |
| 1,363,075 | 12/1920 | Adams . |
| 2,560,712 | 7/1951 | Bell . |
| 3,124,127 | 3/1964 | Ruuska . |
| 3,512,776 | 5/1970 | Thomas, Sr. . |
| 3,533,407 | 10/1970 | Smith . |
| 3,606,319 | 9/1971 | Borden ................... 2/161.1 X |
| 3,670,731 | 6/1972 | Harmon . |
| 3,707,730 | 1/1973 | Slider ........................ 2/161.1 |
| 3,815,908 | 6/1974 | Hashimoto . |
| 3,863,271 | 2/1975 | Moroney ................... 2/161.2 |
| 3,942,535 | 3/1976 | Dragan . |
| 3,971,374 | 7/1976 | Wagner . |
| 4,005,709 | 2/1977 | Laerdal . |
| 4,022,197 | 5/1977 | Castiglia . |
| 4,040,632 | 8/1977 | Pawl . |
| 4,071,913 | 2/1978 | Rector ..................... 2/161.1 X |
| 4,081,150 | 3/1978 | Tyson . |
| 4,190,054 | 2/1980 | Brennan ..................... 607/112 |
| 4,190,906 | 3/1980 | Patton, Jr. ................... 2/162 |
| 4,374,439 | 2/1983 | Norman ...................... 2/162 |
| 4,436,089 | 3/1984 | Schmid . |
| 4,441,490 | 4/1984 | Nirschl . |
| 4,470,417 | 9/1984 | Gruber ...................... 607/108 |
| 4,554,317 | 11/1985 | Behar et al. . |
| 4,558,694 | 12/1985 | Barber ........................ 602/21 |
| 4,584,993 | 4/1986 | Nelson . |
| 4,747,163 | 5/1988 | Dzierson .................... 2/161.1 |
| 4,748,975 | 6/1988 | Yashima . |
| 4,841,962 | 6/1989 | Berg et al. . |
| 4,881,533 | 11/1989 | Teurlings ..................... 602/21 |
| 4,934,357 | 6/1990 | Frantzich et al. . |
| 4,971,047 | 11/1990 | Kanzler et al. . |
| 5,014,689 | 5/1991 | Meunchen et al. . |
| 5,065,752 | 11/1991 | Sessions et al. . |
| 5,115,801 | 5/1992 | Cartmell et al. . |
| 5,135,518 | 8/1992 | Vera . |

FOREIGN PATENT DOCUMENTS 2650175  2/1991  France .................... 602/21

Primary Examiner—Robert Bahr
Assistant Examiner—Linda C. M. Dvorak
Attorney, Agent, or Firm—Pravel, Hewitt, Kimball & Krieger

[57] ABSTRACT

The present invention relates to a gel shell splint for the hand which has an elongated support constructed of an elastomeric material that is shaped to fit the center portion of a human hand. The support is releasably secured around the hand with the support being secured on either the dorsal or palmar side of the hand. A rigid shell shaped to fit the center portion of the hand is releasably secured to the interior side of the support and a compressible pad is attached to the interior side of the shell.

10 Claims, 2 Drawing Sheets

GEL SHELL SPLINT

FIELD OF THE INVENTION

This invention relates to a splint that cushions and protects a human hand following an injury, repetitive impact trauma, or pre- or post- surgical procedures.

BACKGROUND OF THE INVENTION

Surgery due to tendon, ligament, or bone repair in any part of the hand or carpal tunnel surgery in the palmar area of the hand frequently results in persistent pain in the area of the incision. Cumulative trauma disorder or repetitive impact trauma in the palm can also cause great discomfort resulting in incapacity of the hand.

Pain and discomfort is aggravated as pressure is applied to the affected area during attempted use of the hand. Because patients tend to be reluctant to use their hand when there is pain, rehabilitation time is longer. Generally, scar tissue at an incision site becomes remodeled, softens and pain resolves over time. However, when a scar is formed in an area of the hand, individuals are extremely hypersensitive to touch or impact pressure on this area even when the wound is healed.

Devices commonly used to protect the hand include elastic bandages and various types of padded gloves. Although they provide protection and support, these devices do not provide a solid barrier against physical contact or disperse the energy created as forces are applied to the hand during normal use.

The splint of the present invention is designed to protect the sensitive and painful area of the hand while still allowing full motion of the hand and digits. Following surgery or trauma to the hand the invention allows a patient to start using his or her hand sooner and shortens the time required for rehabilitation by decreasing pain and preventing hypertrophic scar formation.

SUMMARY OF THE INVENTION

Before describing the invention, definitions of relevant descriptive terms relating to the hand would be useful. The proximal area of the hand refers to the portion of the hand near the wrist; the distal area of the hand to the portion of the hand near the fingers; the radial side refers to the thumb side of the hand; the ulnar side to the side of the hand away from the thumb; the palmar portion of the hand to the inside of the hand at the palm; and the dorsal side of the hand refers to the back of the hand.

The gel shell splint of the present invention solves the problems discussed above by providing a splint which facilitates healing by cushioning and protecting injuries or incisions in the affected area of the hand. The splint of the subject invention is generally formed of separate three parts, an outer support, a rigid shell, and an inner pad.

The outer support is constructed of a woven elastomeric material and is shaped to fit the center portion of a human hand. The support is generally rectangular in shape with one end being elongated to extend around the side of the hand opposite the thumb to the other side of the hand. The other end of the support is formed into two narrow straps that extend around the thumb side of the hand, each strap wrapping around opposite sides of the thumb. The narrow straps engage the elongated end on the opposite side of the hand and are attached to each other through a VELCRO ® type fastening system.

The rigid shell section is attached to the side of the support lying next to the skin with a VELCRO ® type fastening system. The shell is formed of a low temperature plastic material that protects the affected area from direct impact. In a preferred embodiment, the shell is contoured to fit the center portion of the palm and accordingly is generally triangular in shape.

The inner pad is placed between the skin of the hand and the rigid shell. It is also shaped to fit the contour of the shell section and is adhered to one side of the shell. The pad is preferably formed of a water or mineral based gel material which helps to disperse energy caused by external pressures or blows to the affected area of the hand. The gel pad also helps to desensitize an incision site and prevent hypertrophic scar formation.

The gel shell splint of the present invention can be used after surgery in which an incision is made to the palmar or dorsal side of the hand. Surgery of this kind includes tendon, ligament, or bone repair, carpal tunnel release surgery, or biopsy incisions. The splint can also be used for cumulative trauma disorder or any other preventative splinting where protection from repetitive impact or vibration is indicated.

In an alternate embodiment, the splint can be used on portions of a human arm either in its present form or with modifications to the outer support and the shell.

BRIEF DESCRIPTION OF THE DRAWINGS

The invention will become more apparent when the detailed description of an exemplary embodiment set forth below is considered in conjunction with the appended drawings in which.

DETAILED DESCRIPTION OF AN EXEMPLARY EMBODIMENT

Figure 1:
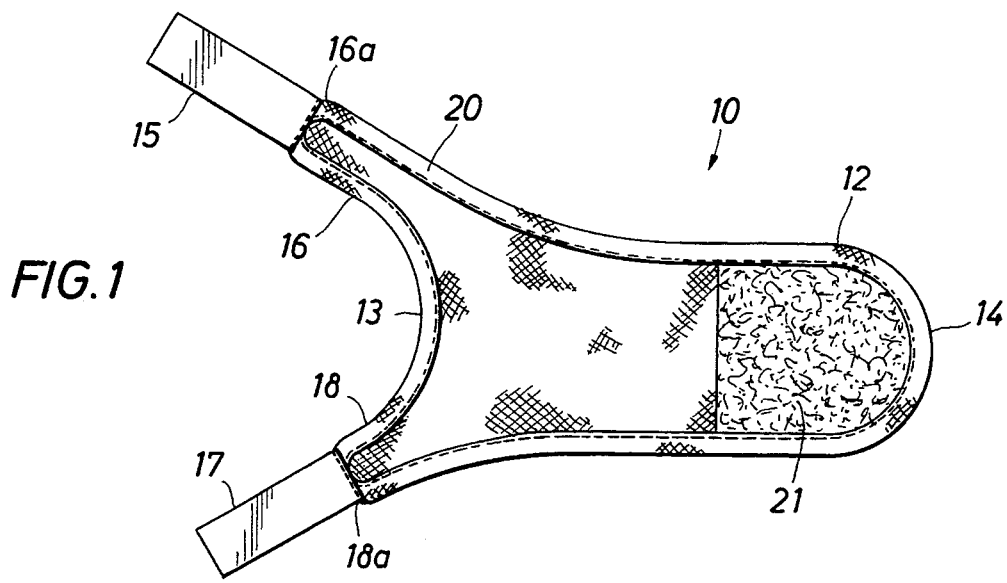
FIG. 1 is a plan view of the exterior side of a fabric support according to the present invention.

As shown in FIGS. 1-6, a gel shell splint 10 includes a support 12, a rigid shell 30 and an inner pad 40. The support 12 is generally rectangular in shape and is formed of an elastomeric material. The support 12 is shaped to fit the center portion of a human hand and has a rounded end 14 and an opposite end 13 shaped to fit around a thumb T of a human hand H. The end 13 extends into two narrow straps, a distal strap 16 and a proximal strap 18 which wrap around the thumb T to the dorsal side D of the hand when the splint 10 is centered on the palmar side P of a hand H.

Figure 2:
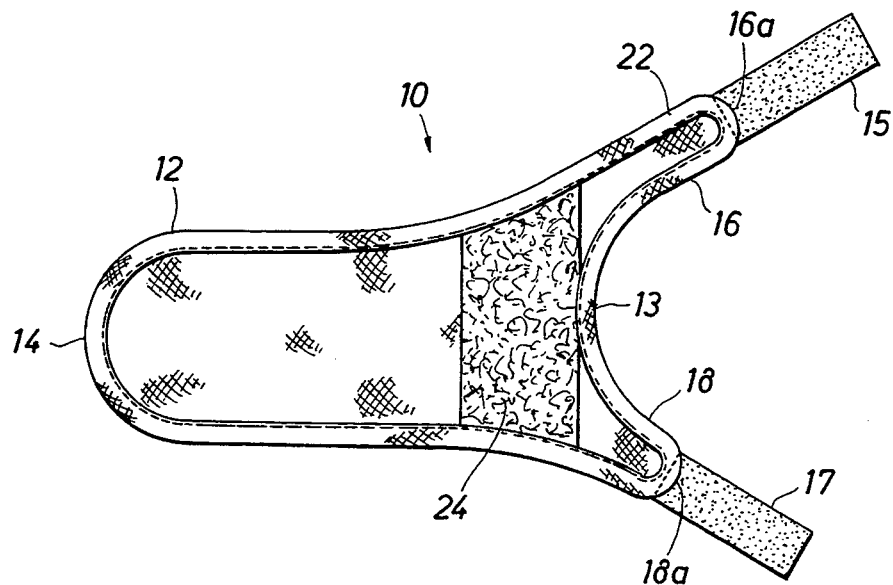
FIG. 2 is a plan view of the interior side of the support in FIG. 1.

The support 12 has an exterior side 20 facing away from the hand and an interior side 22 facing the hand, as shown in FIGS. 1 and 2. A fastener 21, formed of a loop gender material of a VELCRO ® type fastening system, is attached on the exterior side 20 of the support 12 adjacent the rounded end 14. The fastener 21 is about 2.50 inches across and is the width of the support 12 at the rounded end 14.

A fastener 15 is attached to the strap 16 at strap end 16a, and a fastener 17 is attached to the strap 18 at the strap end 18a for engagement with the fastener 21 on the exterior side 20 of the support 12. The fasteners 15 and 17 are formed of a material that is suitable for the hook gender of a VELCRO ® type fastening system. As illustrated in FIG. 2, the hook gender portion of the fasteners 15 and 17 is on the interior side 22 of the support 12.

Figure 7:
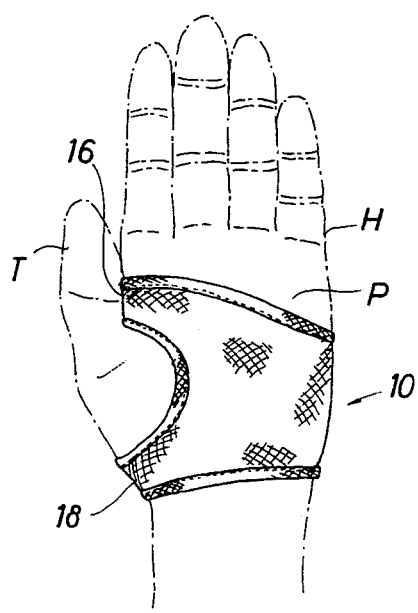
FIG. 7 is a perspective view illustrating the splint of FIG. 6 applied to the palmar side of a human hand.
Figure 8:
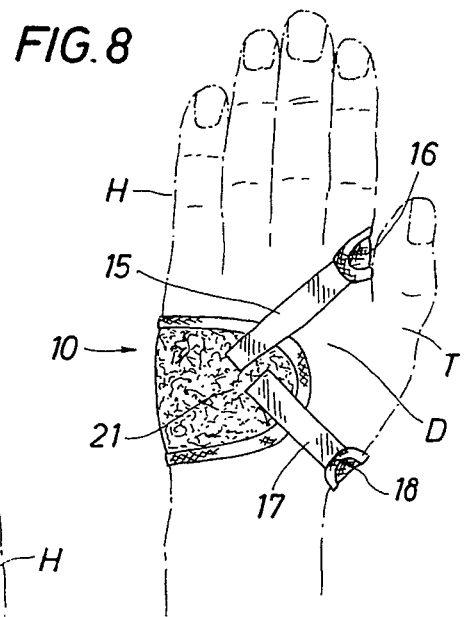
FIG. 8 is a perspective view illustrating the splint of FIG. 7 as viewed from the dorsal side of the hand.

In a preferred embodiment, the splint 10 is positioned on the hand H by placing the support 12 in the palm P of a hand H and wrapping the distal strap 16 through the web space on the radial side of the hand and wrapping the proximal strap 18 around the base of the thumb T, as illustrated in FIG. 7. The rounded end 14 wraps around the ulnar side of the hand H to the center of the dorsal side D of the hand. As shown in FIG. 8, the fasteners 15 and 17 engage with the fastener 21 on the exterior surface 20 of the support 12, securing the splint 10 to the hand H.

As shown in FIG. 2, a fastener 24 is attached to the interior side 22 of the support 12, adjacent to the end section 13, for attaching the shell 30 to the support 12. The fastener 24 is formed of a loop gender material of a VELCRO ® type fastening system and in a preferred embodiment is about 1.25 inches across and the width of the support 12.

Figure 3:
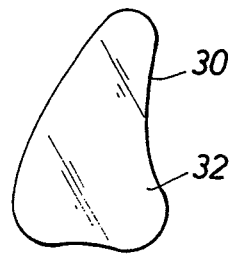
FIG. 3 is a plan view of the interior side of a hard shell according to the present invention.
Figure 4:
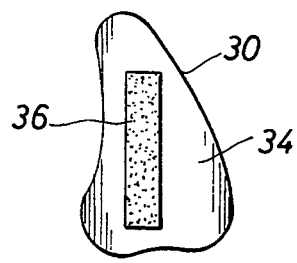
FIG. 4 is a plan view of the exterior side of the shell of FIG. 3.

The rigid shell 30, as illustrated in FIGS. 3 and 4, protects the affected area of the hand from direct impact. In a preferred embodiment, the shell 30 is generally triangular in shape and is molded to fit the contours of the center portion of the palm with a concave portion facing the palm. The shell 30 is formed of a thermoplastic material that is approximately 1/16 of an inch thick and in a preferred embodiment, is made of Polyform ® Light, a product of Smith & Nephew Rolyan, Inc.

The shell 30 has an interior side 32 and an exterior side 34. A fastener 36, formed of a hook gender material of a VELCRO ® type fastening system, is attached to the exterior side 34 of the shell 30. The fastener 36 is centered along the midline of the exterior side 34 of the shell 30 and is about 0.50 inches wide and 2.0 inches long. The hook gender material of the fastener 36 engages with the loop gender material of the fastener 24 and releasably secures the shell 30 to the interior side 22 of the support 12.

Figure 5:
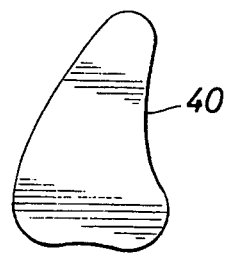
FIG. 5 is a plan view of an inner pad according to the present invention.

The inner pad 40 is shown in FIG. 5. It is shaped to conform to the shape of the shell 30 and is permanently attached to the interior side 32 of the shell 30. The inner pad 40 is formed of a gel-like, compressible material. Such a material is formed of a cross-linked three dimensional polymer formulated with a water or mineral base. In a preferred embodiment, the gel pad 40 is formed of Silpos ®, a product of the Silpos Company, Buffalo, N.Y. and is die cut into the appropriate shape. The gel pad 40 provides additional protection from impact by dispersing energy resulting from external pressures on the palm. The gel material of the pad 40, which is next to the skin, also provides a constant light pressure to the incision site which helps to desensitize the area and prevent hypertrophic scar formation.

Figure 6:
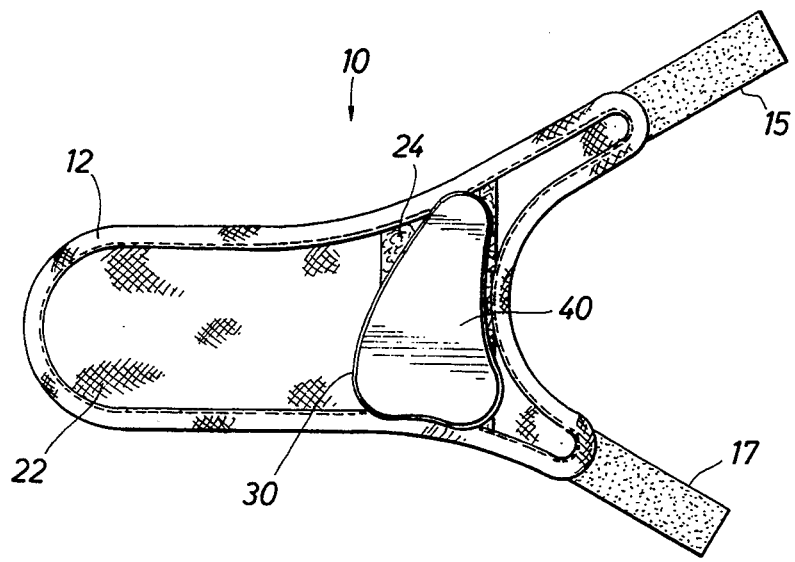
FIG. 6 is a plan view of the splint of the present invention.
Figure 9:
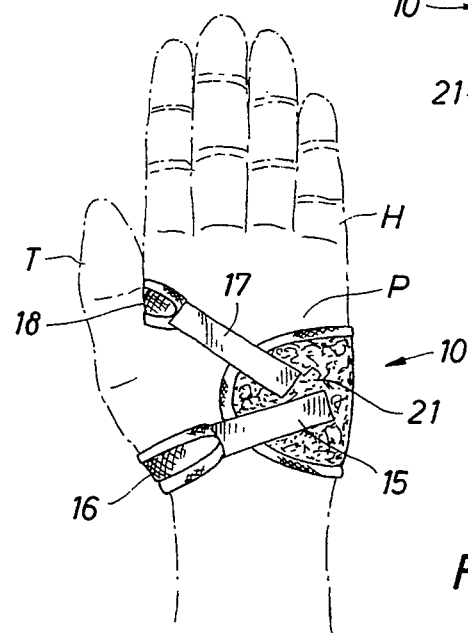
FIG. 9 is a perspective view illustrating the splint of FIG. 6 applied to the dorsal side of a human hand.

The assembled gel shell splint 10 is illustrated in FIG. 6. The gel pad 40 is joined to the interior side 32 of the shell 30 which, in turn is releasably attached to the support 12. FIG. 7 shows the splint 10 secured around the palmar side of a human hand H and FIG. 9 shows the splint 10 secured around the dorsal side of a human hand H. Following surgery or trauma to the hand, the gel shell splint allows a patient to start using his or her hand sooner and shortens rehabilitation time by decreasing pain and preventing hypertrophic scar formation.

Although the present invention has been described with reference to its preferred embodiments, those skilled in the art will recognize changes which may be made in form or structure which do not depart from the spirit of the invention already described in the specification and embodied in the claims which follow.

What is claimed is:

1. A gel shell splint for the hand, comprising:
  a) support means for covering at least part of the center region of a human hand;
  b) first securing means for releasably securing the support means to the hand;
  c) a shell formed of a rigid material shaped and dimensioned to fit in the center region of a human hand with a generally concave portion facing the hand;
  d) a pad formed of a compressible material shaped and dimensioned to fit in the concave portion of the shell, wherein said pad is in direct contact with the skin of the hand when the splint is positioned on the hand of the user; and
  e) a second securing means for releasably securing the side of the shell opposite the concave portion to the support means.

2. The splint of claim 1, wherein the support means is generally rectangular in shape with a rounded end adapted to extend around the side of the hand opposite the thumb to the other side of the hand.

3. The splint of claim 2, wherein the support means include a pair of narrow straps adapted to extend around opposite sides of the thumb to the other side of the hand.

4. The splint of claim 3, wherein the securing means includes material having hook and loop genders of a fastening system attached to the rounded end and the narrow straps.

5. The splint of claim 1, wherein the pad includes attachment means for attaching the pad to the shell.

6. The splint of claim 1, wherein the shell is formed of a thermoplastic material.

7. The splint of claim 1, wherein the second securing means includes material having hook and loop genders of a fastening system.

8. The splint of claim 1, wherein the pad means is formed of a water or mineral based gel material.

9. A gel shell splint for the hand, comprising:
  a) a support means constructed of an elastomeric material, generally rectangular in shape with a rounded end and an opposite end, the opposite end including a pair of narrow straps adapted to extend around opposite sides of the thumb to the back of the hand, and the support means having an interior and an exterior side;
  b) first securing means for releasably securing the support means around the hand, the support means adapted to be secured on the dorsal side of the hand;

c) a rigid shell formed of a rigid material 13 shaped and dimensioned to fit in the palmar region of a human hand with a generally concave portion facing the hand, the shell having an interior and an exterior side, and second securing means for releasably securing the exterior side of the shell to the interior side of the support; and d) a pad formed of a water or mineral based gel material shaped and dimensioned to fit in the concave portion of the shell, the pad being attached to the interior side of the shell, wherein said pad is in direct contact with the skin of the hand when the splint is positioned on the hand of the user.

10. A gel shell splint for the hand, comprising:

a) a support means constructed of an elastomeric material, generally rectangular in shape with a rounded end and an opposite end, the opposite end including a pair of narrow straps adapted to extend around opposite sides of the thumb to the palmar side of the hand, and the support means having an interior and an exterior side;

b) first securing means for releasably securing the support means around the hand, the support means adapted to be secured on the palmar side of the hand;

c) a rigid shell formed of a rigid material shaped and dimensioned to fit in the center region of the dorsal side of a human hand with a generally concave portion facing the hand, the shell having an interior and an exterior side, and second securing means for releasably securing the exterior side of the shell to the interior side of the support; and d) a pad formed of a water or mineral based gel material shaped and dimensioned to fit in the concave portion of the shell, the pad being attached to the interior side of the shell, wherein said pad is in direct contact with the skin of the hand when the splint is positioned on the hand of the user.

* * * * *